United States Patent [19]

Utterberg

[11] Patent Number: 5,385,372
[45] Date of Patent: Jan. 31, 1995

[54] LUER CONNECTOR WITH INTEGRAL CLOSURE

[76] Inventor: David S. Utterberg, 2033 First Ave., #3 Seattle, Wash. 98121

[21] Appl. No.: 2,778

[22] Filed: Jan. 8, 1993

[51] Int. Cl.[6] .................. A61M 25/00; A61M 5/32
[52] U.S. Cl. ...................... 285/332; 285/901; 285/391; 604/263; 604/905; 220/337; 220/339; 215/306
[58] Field of Search .............. 604/263, 905, 192; 285/332, 901, 322, 391; 220/337, 339; 215/306

[56] References Cited

U.S. PATENT DOCUMENTS

| | | | |
|---|---|---|---|
| 3,633,586 | 1/1972 | Sheridan | 285/901 |
| 3,741,217 | 6/1973 | Clarke | 285/901 |
| 4,534,483 | 8/1985 | Kassis et al. | 220/337 |
| 4,655,363 | 4/1987 | Neat | 215/306 |
| 4,674,640 | 6/1987 | Asa et al. | 215/306 |
| 4,713,219 | 12/1987 | Gerken et al. | 220/339 |
| 4,781,697 | 11/1988 | Slaughter | 604/263 |
| 4,817,991 | 4/1989 | Frentzel et al. | 285/901 |
| 4,963,132 | 10/1990 | Gibson | 285/901 |
| 4,982,842 | 1/1991 | Hollister | 604/263 |
| 5,047,021 | 9/1991 | Utterberg | 285/332 |
| 5,065,783 | 11/1991 | Ogle, II | 604/905 |
| 5,071,413 | 12/1991 | Utterberg | 604/905 |
| 5,078,693 | 1/1992 | Shine | 604/192 |
| 5,098,405 | 3/1992 | Peterson et al. | 604/256 |
| 5,098,410 | 3/1992 | Kerby et al. | 604/256 |
| 5,213,226 | 5/1993 | Nichols | 220/337 |
| 5,225,165 | 7/1993 | Perlman | 215/306 |
| 5,242,417 | 9/1993 | Paudler | 604/263 |
| 5,254,314 | 10/1993 | Yu et al. | 220/339 |
| 5,259,843 | 11/1993 | Watanabe et al. | 604/905 |

FOREIGN PATENT DOCUMENTS

0460821A1 12/1991 European Pat. Off. .
9211884 7/1992 WIPO ................ 604/192

Primary Examiner—Eric K. Nicholson
Attorney, Agent, or Firm—Gerstman, Ellis & McMillin, Ltd.

[57] ABSTRACT

A female luer connector comprises a tube having an open, outer end in a luer-tapered bore communicating with the outer end. The tube carries a side arm that from a positioned spaced longitudinally from the open, outer end, with the side arm extending both radially outwardly from the tube and in generally longitudinal relationship with the axis of the bore toward the open, outer end, to define a space between the tube and the side arm for receiving an outer, threaded sleeve of a male luer lock connector. A cap is connected to the side arm through a plastic hinge in a position permitting the cap to pivot between a closed position in which the cap closes the open, outer end, and an open position in which the cap is spaced from the open, outer end. The side arm defines an effectively rigid, fixed configuration to position the hinge and cap to naturally and spontaneously permit pivoting to the closed position to the open position, typically upon pressing with a single finger.

20 Claims, 2 Drawing Sheets

LUER CONNECTOR WITH INTEGRAL CLOSURE

BACKGROUND OF THE INVENTION

Luer connectors are well-known and used in a wide variety of medical sets and the like, in which a tapered sleeve or nozzle fits into a tapered socket to provide a tight connection. Typically, the luer connector complies with ISO/ANSI specifications.

Often, a "luer-lock" connector is used, in which the conventional luer connection is reinforced with an outer sleeve carried on one of the connectors, typically the male connector, which sleeve engages outwardly extending projections of the female luer connector in threaded, interlocking relation, to provide assurance that the luer connection does not accidentally separate.

Such luer connectors and luer lock connectors come in a wide variety of designs, and are used as connectors for parenteral solution sets, blood sets for dialysis and other medical procedures, connectors for joining hypodermic needles and needle hubs, and the like.

Female luer connectors in the prior art originally had separate closure caps. Such a design is of course relatively costly to mold and assemble, there being two separate parts, and often the caps would be lost or would fall on the floor.

Then, as a next step in the prior art, female luer connectors were molded with integral caps attached by a hinge. However, these connectors were not suitable for mating with male luer lock connectors, because the outside threaded skirt of the typical male luer lock connector would often be impeded by the hinge.

As another developmental step, luer connectors were provided in which the cap is attached by an umbilical cord-like strap which connects to the female connector at a position that is spaced from the open end thereof. Problems with the system included the fact that when the connector is uncapped, the cap is free to move in any direction that its flexible cord permits. Thus, due to the flexibility of such an umbilical cord-like strap, this system is ill suited for automated capping, and thus requires manual labor to initially place the cap on the end of the connector after molding. Also, when the user has removed the cap and desires to recap it, the recapping is not easily done with a single finger of the same hand holding the connector, but rather more often requires closer attention and grasping of the cap with the thumb and forefinger of the other hand to properly position the cap for recapping on the luer.

By this present invention, a luer with a hinged cap is provided in which, in preferred embodiments, the hinged cap may be removed from the luer with the action of a single finger of the same hand holding the luer connector, and it may be reapplied in a reliable, repetitive manner with a single finger as well.

The luer connector of this invention may be integrally molded in a single shot with its cap, but, nevertheless, the cap may be placed on the end of the luer connector in automated manner, for reduction of initial manufacturing costs. Also, the cap is manually removed, with ease in preferred embodiments with the action of single finger, and the cap may also be replaced with the action of a single finger in the most preferred embodiments. Additionally, a space is provided so that a male luer lock connector may connect with the female luer connector of this invention, with the locking sleeve of the typical luer lock connector engaging in unimpeded manner with the exterior of the female luer connector.

DESCRIPTION OF THE INVENTION

In accordance with this invention a luer connector is provided, which comprises a tube having an open, outer end and a luer-tapered surface communicating with the outer end. The tube carries a side arm, which side arm extends both radially outwardly from the tube from a position longitudinally spaced from the open, outer end and also extends in generally longitudinal relationship with the axis of the bore of the tube toward the open outer end, to define a space between the tube and the side arm which a locking sleeve of a male luer-lock connector can occupy.

A cap is connected to the side arm by hinge means in a position permitting the cap to pivot between a closed position in which the cap closes the open, outer end, and an open position in which the cap is spaced from the outer end. Thus the hinge is radially outwardly spaced from the luer connector tube, typically by just the right amount so that folding of the hinge causes the cap to enter into the closed position.

The side arm defines an effectively rigid, fixed configuration to position the hinge and cap, to naturally and spontaneously permit pivoting to the closed position from the open position upon pressing of the cap, typically with a single finger.

In one preferred design, the side arm has a first portion which extends primarily radially outwardly from the tube at the position which is longitudinally spaced from the open, outer end, typically by about 4 to 20 mm.

Second side arm portion is carried by the first portion, and extends primarily in generally longitudinal relationship with the axis of the bore toward the open, outer end, so that the aforementioned space between the tube and second portion is defined, to provide room for a locking sleeve of a luer-lock connector. The cap is then connected to typically the outer end of the second side arm portion by hinge means in a position permitting the cap to pivot between the closed and open positions as discussed above.

The typical hinge means is a living hinge formed from polypropylene plastic or the like, with the entire luer connector, cap and side arm being integrally molded in a single molding shot. Any appropriate plastic which is capable of providing an integral hinge may be used.

Typically at least the second portion of the side arm has a width which is at least twice the thickness of the side arm, measured in a radial direction relative to the tube. Thus, the side arm comprises a band, typically a rather rigid band, to resist rotational stresses and to position the hinge and cap in a desired location so that it readily pivots between the closed and open positions.

Sometimes the luer connector of this invention may be made of a softer material such as polyvinyl chloride plastic. In this case, the side arm typically is less rigid then a similar connector made out of polypropylene plastic. However, it is the intention of this invention for the side arm to have sufficient rigidity to substantially accomplish the purposes of this invention as described above. Such sufficient rigidity is intended to be included in the term "effectively rigid".

To foster the desired rigidity in the side arm, a portion of the side arm, typically including the first portion, may comprise radial fin means extending outwardly from the tube and connecting with the remainder of the side arm to provide added rigidity to the first portion, while the side arm still provides a space for receiving the locking sleeve of typically a male luer lock connector.

It is also preferred in some designs for the cap to define a projection extending outwardly from a side of the cap, the projection being connected to the hinge. The length of this projection may be designed to cause the cap to reliably and consistently pivot between the closed and open positions as described above without the need for manual positioning, so that the cap may be opened or closed with a single finger, with little concentration or manual manipulation on the part of the user. To facilitate this, a handle may project outwardly from the cap, and typically from the projection discussed above, in transverse relation thereto. This handle may be used to facilitate particularly the opening of the cap out of the closed position, typically with a single finger.

DESCRIPTION OF SPECIFIC EMBODIMENTS

Figure 1:
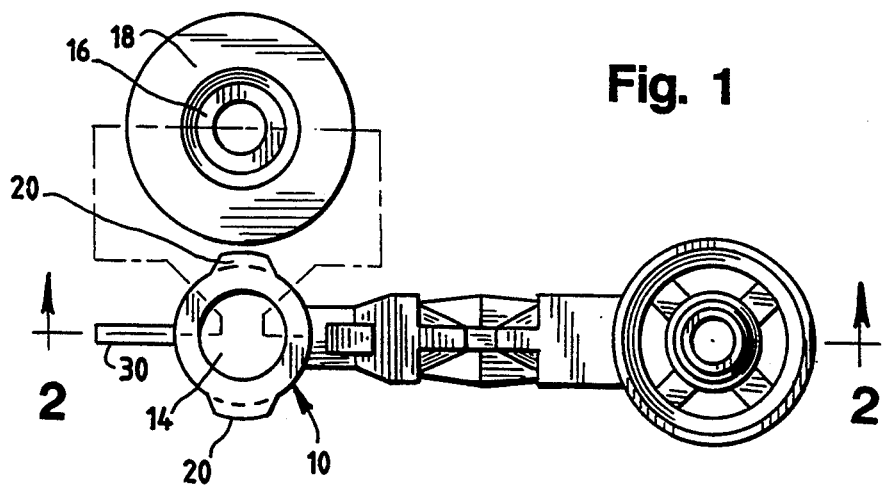
FIG. 1 is an enlarged, plan view of a female luer connector in accordance with this invention, with an attached cap in an open position spaced from the open, outer end, with a male luer-lock connector also shown.
Figure 2:
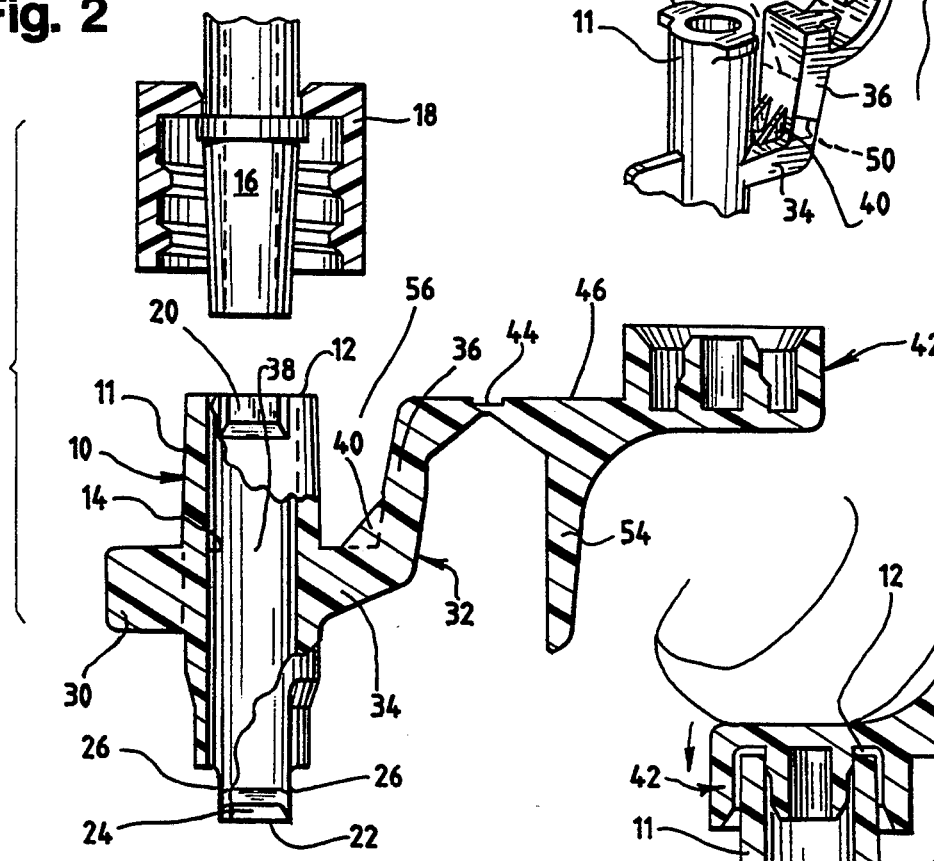
FIG. 2 is a sectional view taken along line 2—2 of FIG. 1.

Referring to FIGS. 1–4, a female luer connector 10 is shown having a tube 11 which has an open outer end 12 and a luer-tapered bore 14 of conventional design, for connection with a male luer connector 16. Male luer connector 16 is shown in FIGS. 1 and 2 to be of the luer lock type, having a surrounding threaded sleeve 18 of conventional design for interlocking with female connector 10 by means of outwardly projecting bosses 20 carried on the exterior of female connector 10 in a conventional manner.

Figure 2A:
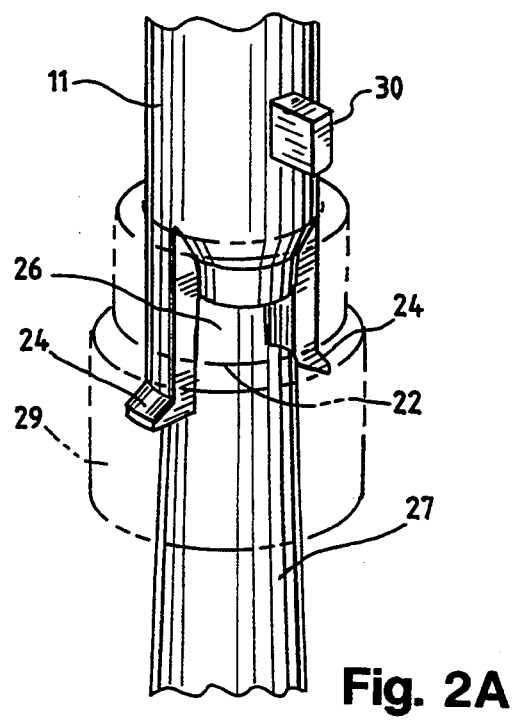
FIG. 2a is a fragmentary view of FIG. 2, rotated by 90 degrees and showing connection with a male luer lock connector.

The specific design of female luer connector shown particularly in FIG. 2a has an open end 22 which is opposed to outer end 12, having outwardly projecting members 24 and longitudinal slots 26 to facilitate connection with a male luer connector 27, which can project into bore 12 through end 22, with a locking sleeve 29 of the luer lock connector engaging projections 24. Thus, by this means, a male luer lock connector may be converted into a female connector, making use of female luer connector 10. Otherwise, end 22 of luer connector 10 may be conventionally shaped to connect with flexible tubing.

Projecting tab 30 is present to facilitate the gripping and turning of luer connector 10 as connections are made and broken.

In accordance with this invention, luer connector 10 carries a side arm 32 which is an integrally molded part of the luer connector system. In this embodiment, side arm 32 defines a first portion 34 extending radially outwardly from the tube of luer connector 10 at a position which is longitudinally spaced by about 1 centimeter from open, outer end 12. A second side arm portion 36 is integrally connected with first portion 34 through an angled area, with second portion 36 extending in generally longitudinal relationship with the axis 38 of bore 14, with second section 36 extending towards said open, outer end 12.

As shown particularly in FIG. 2, the angled area between the first and second portions 34, 36 may be reinforced with an integrally molded fin 40, which promotes the rigidity of side arm portion 32. It is, however, to be understood that side arm portion 32 does not have to be absolutely rigid, but merely to have sufficient rigidity to accomplish the desired purposes of this invention as discussed above.

The second portion 36 of side arm 32 connects to cap 42 by an integral plastic living hinge 44 which may be defined, as is conventionally known, by a thin portion of the plastic, so that preferential bending takes place at hinge 44.

Preferably, cap 42 defines a projection 46 which extends outwardly from a side of the cap, with projection 46 being connected to hinge 44. The length of projection 46 may be carefully designed so that, as cap 42 is rotated about hinge 44, it naturally enters into the desired, closed position which is particularly illustrated in FIG. 4.

Side 32 arm generally, and particularly the second portion 36 thereof, may be the shape of a band having a width 48 which is preferably at least twice the thickness 50 of the side arm portion, measured in the radial direction relative to tube 11. Side arm portion 34 is similarly proportioned, although it is shown to extend in a different direction. Thus, the band shape of the side arm promotes its rigidity, which causes hinge 44 to be positioned at the desired location, where pivoting of cap 42 will cause repeated, reliable, and easy closure of cap 42 onto tube end 12 without having to think about positioning the cap into the right position, as is the usual case in the prior art.

Figure 3:
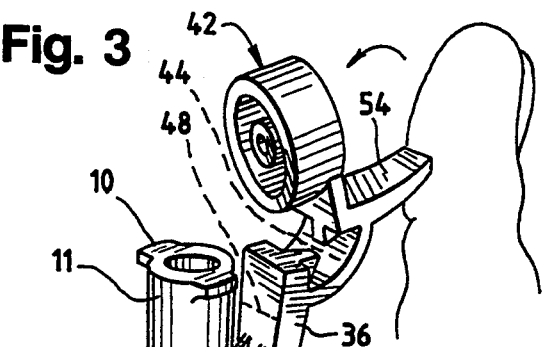
FIG. 3 is a perspective view of the luer connector and integral cap of FIG. 1, showing the cap in the process of being pivoted from an open position to the closed position.
Figure 4:
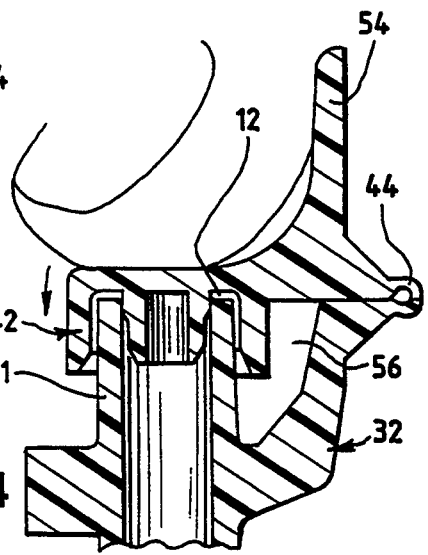
FIG. 4 is a fragmentary, elevational view showing the luer connector of FIG. 1 with the cap in closed position.

Cap 42 also defines a generally rigid handle 54, which can be used to move the cap by pivoting between the closed and open positions, typically with the use of a single finger as shown for example in FIG. 3. Thus, the opening of cap 42 becomes a simple matter simply by the pushing with a single finger of handle 54, causing cap 42 to smoothly pivot off of the end 12 of tube 11. Because of the rigidity of the system and the band shape of side arm 32, the hinge 44 is normally properly positioned under all circumstances so that cap 42 may be pivoted back and forth into closed and open positions with the action of a single finger, with typically the finger operating against handle 54. If desired, as shown in FIG. 4, the finger is also pressing cap 42 into final, seated configuration, although this is optional, and can often be dispensed with.

It can also be seen that hinge line 44 is positioned substantially laterally of the outer end 12 of female luer connector, to facilitate the operation of the device. Side arm 32 and tube 11 define a space 56 between them which serves to receive sleeve 18 of the male luer lock connector, so that the connector 10 of this invention can be used either with male luer connectors or male luer lock connectors.

Preferably, luer connector 10 and cap 42 may be made of polypropylene or the like and formed in a single molding shot, for good functioning of hinge 44, while the remainder of the system is substantially rigid.

Figure 5:
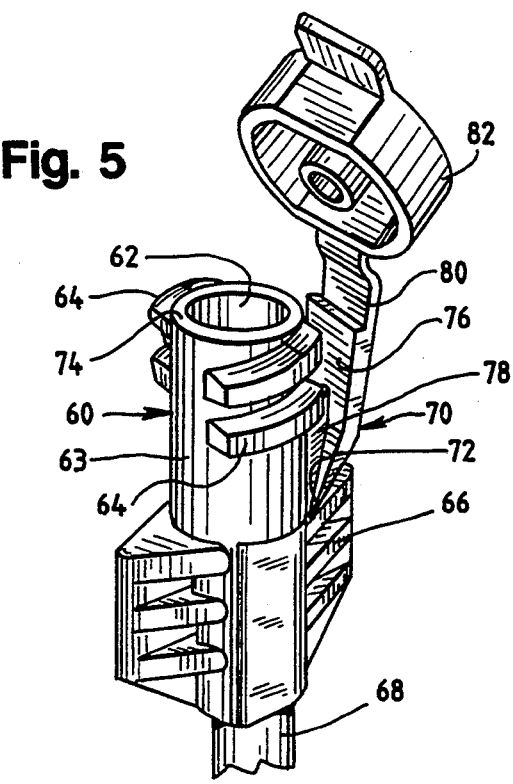
FIG. 5 is a perspective view of another embodiment of female luer connector and integral cap of this invention, with the cap shown in an open position.
Figure 6:
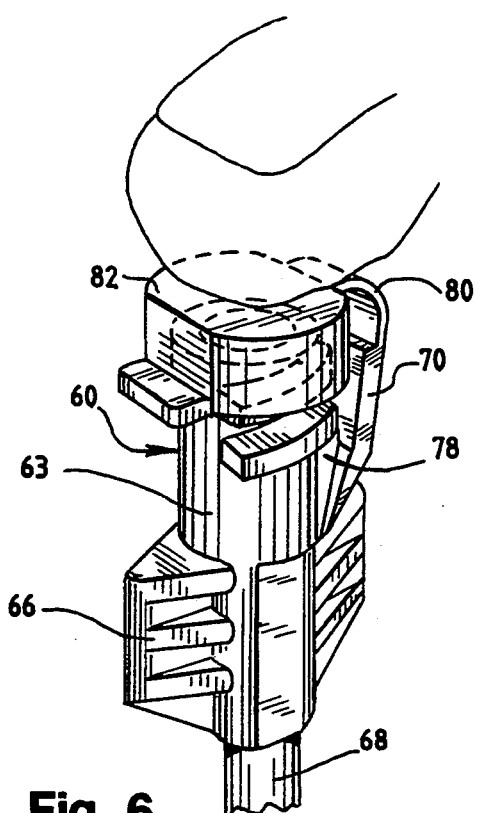
FIG. 6 is a perspective view similar to FIG. 5 showing the cap in the closed position.

Referring now to FIGS. 5 and 6, another design of luer connector in accordance with this invention is disclosed.

Female luer 60 comprises a tube 63 having a tapered bore 62 of conventional design for receiving a male luer or luer lock connector. Female luer 60 is shown to carry interrupted helical threads 64 for connection with the threaded sleeve of an attached luer lock connector.

Side projections 66 are provided to facilitate gripping and twisting of luer connector 60. Plastic tubing 68 can fit into and be sealed within the end of bore 62 which is opposite to the end 74 that carries helical threads 64. Plastic tubing 68 may then be part of any desired medical fluid flow set for blood, parenteral solutions, or the like, such as arterial or venous blood sets for hemodialysis.

In accordance with this invention, luer connector 60 defines an integral side arm 70 which is shown to extend radially outwardly from the tube 63 of connector 60 from a position 72 which is longitudinally spaced by about 1 centimeter from the open, outer end of 74 of tube 63. Also, side arm 70 not only extends radially outwardly, as shown, but it also extends in generally longitudinal relationship with the axis of bore 62 toward, and if desired beyond, open outer end 74 of tube 63. This defines space 76 between tube 63 and side arm 70, which space is present to receive the threaded sleeve of a luer lock connector as the connector engages connector 60 of this invention.

By this invention, it can be seen that side arm 70 is of the shape of a rectangular band in cross section, with the width of side arm 70 being substantially greater than the thickness thereof, which thickness is measured in the radial direction relative to tube 63. Also, a radial fin 78 is provided between tube 63 and side arm 70 adjacent the junction between members 63, 70, and leaving room for space 76 for receiving a connector looking sleeve, as before. Thus, side arm 70 is substantially rigid in structure, being reinforced by its rectangular cross section and the presence of radial fin 78, even when the connector 60 and side arm 70 are integrally molded out of a soft material such a polyvinyl chloride plastic. The amount of rigidity is at least sufficient to accomplish the purposes of this invention as previously described, although of course soft, polyvinyl plastic will not be absolutely rigid.

An integral, thin plastic section 80 is provided at the outer end of side arm 70, which thin section is integrally attached to plastic cap 82. Cap 82 may be of generally conventional design except as otherwise shown and discussed here. Thus, cap 82 may be pivoted about a hinge line that is spontaneously defined in section 80 by use, while side arm 70 remains substantially rigid. The effect of this is to control the path of pivoting of cap 82 so that it, in substantially automatic, spontaneous manner, travels on a pivoting path between the closed position of FIG. 6 and an open position as illustrated in FIG. 5. It thus becomes possible to open and close cap 82 relative to tube 63 with one finger, since the pivoting path of cap 82 as it moves is substantially governed and positioned by the substantially rigid side arm 70, for great ease of removal of cap 82 and replacement thereof during medical procedures.

Connector 60, with its integral side arm 70, reinforcing fin 78, and cap 82 may be simultaneously molded in a single shot, for the minimizing of manufacturing costs. Because of the rectangular or band like cross section of side arm 76 and reinforcing fin 78, it becomes possible to place cap 82 on the end of tube 63 with automated capping equipment, for further cost savings.

Figure 7:
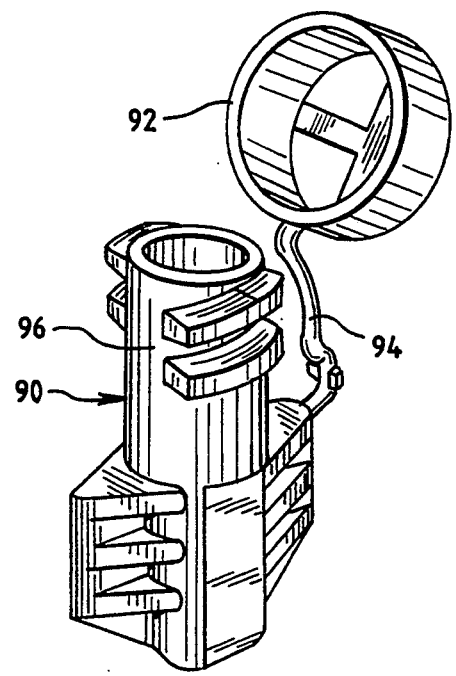
FIG. 7 is a perspective view of a prior art female luer connector which carries an integrally molded cap, the cap being shown in an open position.

By way of comparison, in FIG. 7 there is shown a prior art female luer connector 90 having an integrally molded cap 92 which is connected to luer connector 90 with an integrally molded tether 94. Tether 94 has a width that is not substantially different from its thickness. For this reason, the open position of cap 92, as shown, and its path of motion between the open position and a closed position on luer tube 96, is less strongly and positively controlled when compared with the structures of this invention. Thus it becomes more difficult to use automated equipment to place the cap 92 on tube 96. Similarly, it can be more difficult for the user during a medical procedure to manually replace cap 92 on tube 96, when compared with the structures of this invention, because the path of motion of cap 92 between the "on" and the "off" positions is less strongly constrained.

Also, the function of a hinge in tether 94 is less positively defined, with the pivoting or hinging motion being less focused into a particular hinge line. Rather, in tether 94, most of the entire tether acts as a diffuse-area sort of hinge, with flexing taking place along a substantial portion thereof of typically a centimeter in length or more. This also results in less constraining of the path of motion of lid 92 between open and closed positions.

The above has been offered for illustrative purposes only, and is not intended to limit the scope of the invention of this application, which is as defined in the claims below.

That which is claimed is:

1. A luer connector which comprises a tube having an open, outer end and a luer-tapered surface communicating with said outer end; said tube carrying a side arm which is attached to said tube at a position longitudinally spaced from the open, outer end, said side arm extending from said position radially outwardly from said tube and also extending in generally longitudinal relationship with the axis of said bore toward said open, outer end, to define a space between said tube and said side arm; a cap connected to said side arm by a hinge in a position permitting said cap to pivot between a closed position in which the cap closes said open, outer end and an open position in which said cap is spaced from said open, outer end, said side arm defining an effectively rigid, fixed configuration to position said hinge and cap to permit pivoting to said closed position from the open position upon pressing with a single finger.

2. The luer connector of claim 1 in which said side arm comprises a band extending in said radially outwardly and generally longitudinal relationship, said band having a width at least twice the thickness of said band, said thickness being measured in the radial direction relative to said tube.

3. The luer connector of claim 2 in which radial fin means extend into connection with said band at a portion of said side arm which is longitudinally spaced from the bore open outer end.

4. The luer connector of claim 1 in which said cap defines a projection extending upwardly from a side of said cap, said projection being connected to said hinge.

5. The luer connector of claim 1 in which a handle projects upwardly from said cap, to facilitate opening of the cap out of the closed position with a single finger.

6. The luer connector of claim 1 in which said side arm connects with said tube at a position that is essentially 4 to 20 mm. from said open, outer end.

7. The luer connector of claim 1 in which said side arm comprises a band extending in said radially outward and generally longitudinal relationship, said band having a width of at least twice the thickness thereof, said thickness being measured in the radial direction relative to said tube; radial fin means and connecting with a portion of said side arm that is longitudinally spaced from the open, outer end of the tube to provide added rigidity to said side arm, said cap defining a projection extending radially outwardly from a side of said cap, said projection being connected to said hinge.

8. The luer connector of claim 7 in which a handle projects upwardly from said projection in transverse relation thereto, to facilitate opening of the cap out of the closed position with a single finger.

9. The luer connector of claim 8 in which said side arm connects with said tube at a position that is essentially 4 to 20 mm. from said open, outer end.

10. A female luer connector which comprises a tube having an open, outer end and a luer-tapered bore communicating with said outer end; said tube carrying a side arm having a first portion extending radially outwardly from said tube from a position longitudinally spaced from the open, outer end, and a second side arm portion carried by said first portion and extending in generally longitudinal relationship with the axis of said bore toward said open, outer end, to define a space between said tube and said second portion; a cap connected to said second portion a hinge in a position permitting said cap to pivot between a closed position in which the cap closes said open, outer end, and an open position in which said cap is spaced from said open, outer end; said side arm defining an effectively rigid, fixed configuration to position said hinge and cap to permit pivoting to said closed position from the open position upon pressing with a single finger.

11. The luer connector of claim 10 in which said side arm comprises a second portion which has a width at least twice the thickness of said side arm measured in the radial direction relative to said tube.

12. The luer connector of claim 11 in which said side arm comprises radial fin means connected to and extending outwardly from said tube to provide added rigidity to said first portion.

13. The luer connector of claim 12 in which said cap defines a projection extending radially outwardly from a side of said cap, said projection being connected to said hinge.

14. The luer connector of claim 13 in which a handle projects upwardly from said projection in transverse relation thereto, to facilitate opening of the cap out of the closed position with a single finger.

15. The luer connector of claim 14 in which said side arm connects with said tube at a position that is essentially 4 to 20 mm. from said open, outer end.

16. The luer connector of claim 10 in which a handle projects outwardly from said cap, to facilitate opening of the cap out of the closed position with a single finger.

17. The luer connector of claim 1 in which said tube defines outwardly protruding means for engaging a threaded sleeve of a male luer lock connector.

18. A female luer connector of claim 1 which is an integrally molded plastic piece, said tube having an open end opposed to said open, outer end which is positionable on a male luer connector.

19. A connector which comprises a tube having an open, outer end, a bore of the tube communicating with the outer end, said tube carrying a side arm extending radially outwardly from a position longitudinally spaced from the open, outer end; a cap connected to said side arm and capable of occupying a closed position in which the cap closes the open, outer end and an open position in which the cap is spaced from the open, outer end, said cap connecting to said side arm through an integral plastic hinge, said connector, cap, and side arm being integrally molded from a single piece of plastic, said cap defining a projection extending radially outwardly from a side of said cap, said projection being connected to said hinge, said cap defining a handle projecting upwardly from said cap, to facilitate opening of the cap out of the closed position by manipulation of the handle, said upwardly projecting handle being connected to said projection and extending in transverse relation thereto.

20. The luer connector of claim 11 in which said side arm comprises radial fin means connected to said side arm to provide added rigidity thereto.

* * * * *